United States Patent
Hallinan et al.

(10) Patent No.: US 9,908,833 B2
(45) Date of Patent: *Mar. 6, 2018

(54) REMOVAL OF ALDEHYDES IN ACETIC ACID PRODUCTION PROCESSES

(71) Applicant: LyondellBasell Acetyls, LLC, Houston, TX (US)

(72) Inventors: Noel C. Hallinan, Loveland, OH (US); David L. Ramage, Friendswood, TX (US); Daniel F. White, Houston, TX (US)

(73) Assignee: LyondellBasell Acetyls, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/368,202

(22) Filed: Dec. 2, 2016

(65) Prior Publication Data

US 2017/0158592 A1 Jun. 8, 2017

Related U.S. Application Data

(60) Provisional application No. 62/262,691, filed on Dec. 3, 2015.

(51) Int. Cl.
*C07C 51/12* (2006.01)
*C07C 45/74* (2006.01)
*C07C 51/487* (2006.01)

(52) U.S. Cl.
CPC .............. *C07C 51/12* (2013.01); *C07C 45/74* (2013.01); *C07C 51/487* (2013.01)

(58) Field of Classification Search
CPC ......... C07C 45/45; C07C 45/49; C07C 51/12; C07C 53/08; C07C 45/74; C07C 51/487; C07C 47/21
See application file for complete search history.

(56) References Cited

U.S. PATENT DOCUMENTS

| | | | |
|---|---|---|---|
| 4,701,562 A * | 10/1987 | Olson | .................. C07C 45/002 568/345 |
| 4,704,478 A | 11/1987 | Olson | |
| 7,345,197 B1 | 3/2008 | Hallinan et al. | |
| 7,390,919 B1 | 6/2008 | Salisbury et al. | |
| 8,017,802 B2 | 9/2011 | Scates et al. | |
| 8,076,512 B2 | 12/2011 | Fitzpatrick et al. | |
| 8,114,671 B2 | 2/2012 | Hallinan | |
| 8,293,534 B2 | 10/2012 | Hallinan | |
| 8,969,613 B2 | 3/2015 | Hallinan et al. | |
| 2016/0121320 A1 | 5/2016 | You et al. | |

FOREIGN PATENT DOCUMENTS

| | | | |
|---|---|---|---|
| EP | 2594547 | * | 5/2013 |
| WO | WO-2008016502 A2 | | 2/2008 |
| WO | WO2014/070739 | * | 5/2014 |
| WO | WO-2014070739 A1 | | 5/2014 |
| WO | WO-2014199593 A1 | | 12/2014 |

OTHER PUBLICATIONS

Dumitriu et al, Microporous Materials, 10, pp. 1-12, 1997.
Weili Dai et al, Methanol-to-Olefin Conversion on Silicoaluminophosphate Catalysts: Effect of Bronsted Acid Sites and Framework Structures, ACS Catalysis, vol. 1, No. 4, Apr. 1, 2011, pp. 292-299, XP55279825.
The International Search Report and Written Opinion for PCT/US2016/064759 dated Feb. 13, 2017.

* cited by examiner

*Primary Examiner* — Yevgeny Valenrod
*Assistant Examiner* — Blaine G Doletski

(57) ABSTRACT

The present technology discloses processes for producing carboxylic acid. In some embodiments, the processes include contacting methanol and carbon monoxide in the presence of a liquid reaction medium under carbonylation conditions sufficient to form a carbonylation product, including acetic acid and acetaldehyde. The liquid reaction medium may include a carbonylation catalyst selected from rhodium catalysts, iridium catalysts and palladium catalysts; and water in a water concentration in a range of 1 wt. % to 14 wt. % based on the total weight of the liquid reaction medium. In certain embodiments, the processes comprise contacting at least a portion of the carbonylation product or a derivative thereof with a micro-porous material such as a silicoaluminophosphate (SAPO) to selectively convert at least a portion of the acetaldehyde to crotonaldehyde.

11 Claims, 1 Drawing Sheet

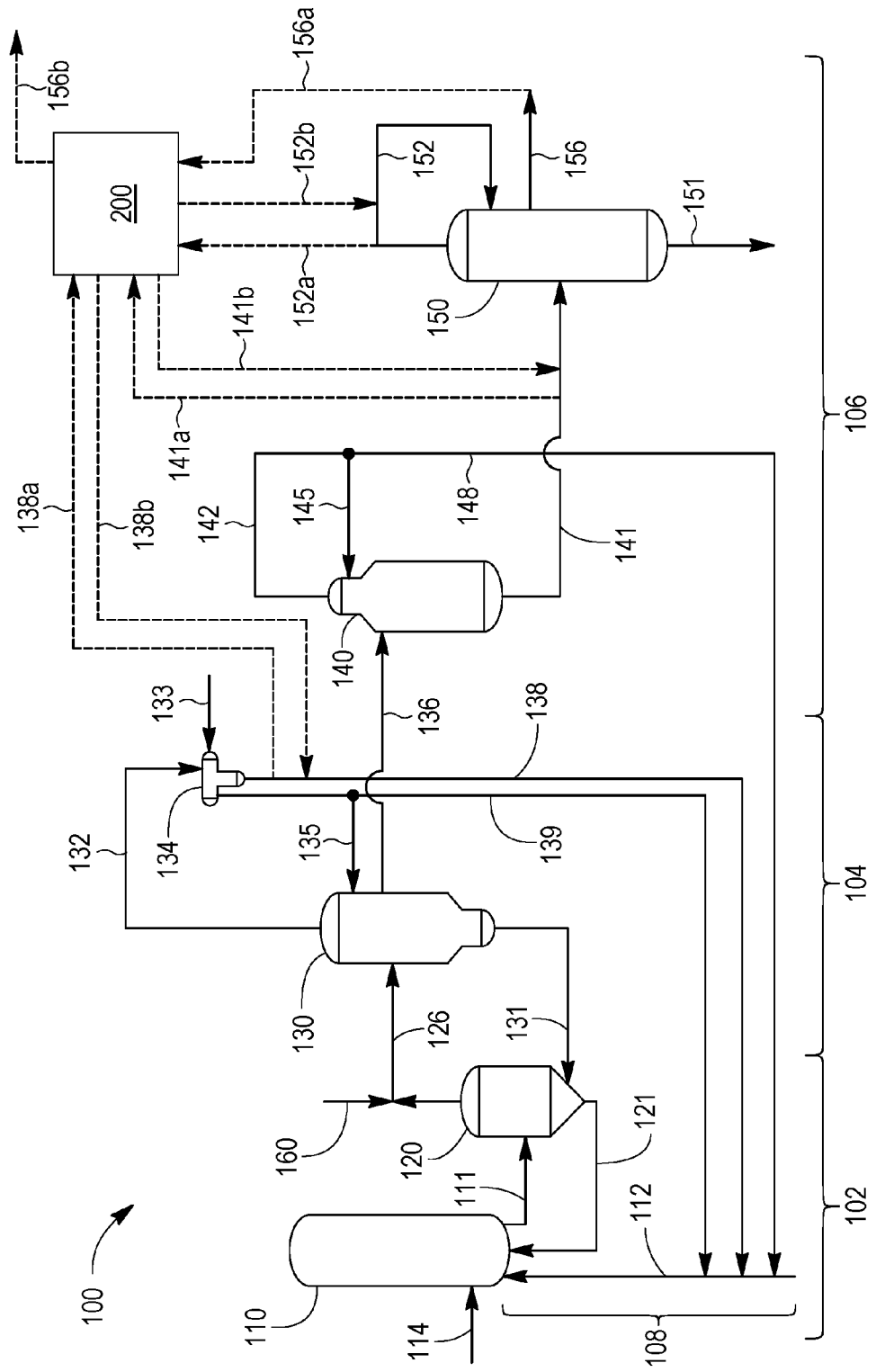

REMOVAL OF ALDEHYDES IN ACETIC ACID PRODUCTION PROCESSES

CROSS-REFERENCE TO RELATED APPLICATIONS

This application claims the benefit of priority to U.S. Provisional Application No. 62/262,691, filed on Dec. 3, 2015, which is incorporated herein by reference in its entirety.

FIELD OF THE INVENTION

The present disclosure generally relates to acetic acid production processes. In particular, embodiments contained herein relate to removal of aldehydes within such processes.

BACKGROUND OF THE INVENTION

This section introduces information from the art that may be related to or provide context for some aspects of the techniques described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Carboxylic acids, such as acetic acid, may be commercially produced by alcohol carbonylation. Unfortunately, carbonylation processes often create by-products, which can be detrimental both to the process at hand, as well as subsequent processes. Significant energy has been devoted to removal of such by-products, including a variety of processes and techniques. However, such processes and techniques can be difficult and costly. The present disclosure provides for processes and related embodiments directed to resolving, or at least reducing, the challenges outlined herein.

SUMMARY OF THE INVENTION

The present disclosure generally includes acetic acid production processes. The processes generally include contacting methanol and carbon monoxide in the presence of a liquid reaction medium under carbonylation conditions sufficient to form a carbonylation product including acetic acid and acetaldehyde, wherein the liquid reaction medium includes: a carbonylation catalyst selected from rhodium catalysts, iridium catalysts and palladium catalysts; and water in a water concentration in a range of 1 wt. % to 14 wt. % based on the total weight of the liquid reaction medium; and contacting at least a portion of the carbonylation product or a derivative thereof with a micro-porous material to selectively convert at least a portion of the acetaldehyde to crotonaldehyde, wherein the micro-porous material includes a silicoaluminophosphate (SAPO).

One or more embodiments include the process of the preceding paragraph, wherein the micro-porous material is represented by the formula $(SiO_2)_x(Al_2O_3)_y(P_2O_5)_z$.

One or more embodiments include the process of any preceding paragraph, wherein the selective conversion exhibits an acetaldehyde to crotonaldehyde conversion of at least 60%.

One or more embodiments include the process of any preceding paragraph, wherein the selective conversion exhibits an acetaldehyde to paraldehyde conversion of less than 1%.

One or more embodiments include the process of any preceding paragraph, wherein the selective conversion is essentially absent acetaldehyde to paraldehyde conversion.

One or more embodiments include the process of any preceding paragraph, wherein the micro-porous material includes an average surface area in a range of 180 $m^2$/g to 550 $m^2$/g.

One or more embodiments include the process of any preceding paragraph, wherein the micro-porous material includes an average pore volume in a range of 0.16 $cm^3$/g to 0.27 $cm^3$/g.

One or more embodiments include the process of any preceding paragraph, wherein the micro-porous material includes a one-dimensional framework of pores absent cages.

One or more embodiments include the process of any preceding paragraph, wherein the micro-porous material includes a Brönsted acidity in a range of 0.1 mmol/g to 0.25 mmol/g.

One or more embodiments include the process of any preceding paragraph, wherein the conversion conditions includes a conversion temperature of about room temperature.

One or more embodiments include the process of any preceding paragraph, wherein the at least a portion of the carbonylation product includes less than 1 wt. % water.

One or more embodiments include the process of any preceding paragraph, wherein the micro-porous material is selected from SAPO-11, SAPO-41, SAPO-46 and combinations thereof.

In one or more embodiments, the process generally includes contacting methanol and carbon monoxide in the presence of a liquid reaction medium under carbonylation conditions sufficient to form a carbonylation product including acetic acid and acetaldehyde, wherein the liquid reaction medium includes: a carbonylation catalyst selected from rhodium catalysts, iridium catalysts and palladium catalysts; and water in a water concentration in a range of 1 wt. % to 14 wt. % based on the total weight of the liquid reaction medium; and contacting at least a portion of the carbonylation product or a derivative thereof with a micro-porous material to selectively convert at least a portion of the acetaldehyde to crotonaldehyde, wherein the micro-porous material includes a silicoaluminophosphate (SAPO), wherein the micro-porous material includes a one-dimensional framework of pores absent cages and a Brönsted acidity in a range of 0.1 mmol/g to 0.25 mmol/g and wherein the selective conversion exhibits an acetaldehyde to paraldehyde conversion of less than 1%.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE DRAWINGS

The claimed subject matter may be understood by reference to the following description taken in conjunction with the accompanying drawings, in which like reference numerals identify like elements, and in which:

The FIGURE illustrates a schematic of one or more embodiments of the disclosed processes.

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION OF THE INVENTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range.

Further, in the description below, unless otherwise specified, all compounds described herein may be substituted or unsubstituted and the listing of compounds includes derivatives thereof.

Some embodiments described herein generally include processes for producing acetic acid. One or more specific embodiments include production of glacial acetic acid (which is encompassed by the term "acetic acid" as referenced herein). Glacial acetic acid refers to acetic acid that is generally undiluted (including a water concentration of up to about 0.15 wt. % based on the total weight of acetic acid and water). In one or more embodiments, the acetic acid production processes generally include carbonylation processes. For example, the acetic acid production processes may include the carbonylation of methanol and/or its derivatives to produce acetic acid.

The carbonylation processes utilized to produce acetic acid generally include reacting an alcohol, such as methanol, with carbon monoxide in the presence of a reaction medium, such as a liquid reaction medium, under carbonylation conditions sufficient to form a carbonylation product including acetic acid and recovering the formed acetic acid from the carbonylation product. As referenced herein, the term "liquid reaction medium" refers to a reaction medium that is substantially liquid in form. For example, the liquid reaction medium contains only minor amounts of alternative phases. In one or more embodiments, the liquid reaction medium is at least 90%, or at least 91%, or at least 92%, or at least 93%, or at least 94%, or at least 95%, or at least 96%, or at least 97%, or at least 98%, or at least 99% liquid phase.

The reaction medium generally includes a carbonylation catalyst. Suitable carbonylation catalysts include, but are not limited to, rhodium catalysts, iridium catalysts and palladium catalysts, for example. Suitable rhodium catalysts include rhodium metal and rhodium compounds selected from rhodium salts, rhodium oxides, rhodium acetates, organo-rhodium compounds, coordination compounds of rhodium and mixtures thereof, for example (see, U.S. Pat. No. 5,817,869, which is incorporated by reference in its entirety). Suitable iridium catalysts include iridium metal and iridium compounds selected from iridium acetates, iridium oxalates, iridium acetoacetates and mixtures thereof (see, U.S. Pat. No. 5,932,764, which is incorporated by reference in its entirety).

The concentration of carbonylation catalyst in the reaction medium may be at least 7.5 mmol, or may be in a range of 1 mmol to 100 mmol, or 2 mmol to 5 mmol, or 2 mmol to 75 mmol, or 5 mmol to 50 mmol, or 7.5 mmol to 25 mmol of catalyst per liter of reaction medium.

In one or more embodiments, the carbonylation catalyst is utilized with a co-catalyst. The co-catalyst may be selected from metals and metal compounds including osmium, rhenium, ruthenium, cadmium, mercury, zinc, gallium, indium, tungsten as well as salts and mixtures thereof. In one or more embodiments, the metal compounds include metal acetates. The concentration of co-catalyst in the reaction medium may be in a range of 500 ppm to 3000 ppm, or 1000 ppm to 2000 ppm, based on the total reaction medium weight, for example.

In one or more embodiments, the reaction medium further includes water. The concentration of water in the reaction medium may be in a range of 1 wt. % to 14 wt. %, or 10 wt. % or less, or 8 wt. % or less, or 6 wt. % or less, or 1 wt. % to 5 wt. %, or 4 wt. % to 8 wt. % based on the total weight of the reaction medium.

Furthermore, the reaction medium may include an alkyl acetate, such as methyl acetate. The concentration of alkyl acetate in the reaction medium may be in a range of 0.6 wt. % to 36 wt. %, or 2 wt. % to 20 wt. %, or 2 wt. % to 16 wt. %, or 3 wt. % to 10 wt. %, or 2 wt. % to 8 wt. % based on the total reaction medium weight, for example.

In addition, it is contemplated that supplemental hydrogen may be supplied to the reaction medium. Supplemental hydrogen may be supplied to the reaction medium to provide a total hydrogen concentration in the gaseous component of the feedstock to the carbonylation reaction in a range of 0.1 mol. % to 5 mol. %, or 0.3 mol. % to 3 mol. %.

In one or more embodiments, the reaction medium further includes one or more promoters. For example, the reaction medium may include an iodide promoter. The iodide promoter may include an alkyl iodide, such as methyl iodide. The concentration of such promoters in the reaction medium may, in some embodiments, be in a range of 0.6 wt. % to 36 wt. %, or 4 wt. % to 24 wt. %, or 6 wt. % to 20 wt. % based on the total weight of the reaction medium. The iodide promoter may be introduced to the reaction medium in a form such that the introduced compound will directly promote the carbonylation reaction, e.g., the introduction of methyl iodide to the carbonylation reaction. Alternatively, one or more compounds may be introduced to the reaction medium to form in-situ generated compounds capable of promoting the carbonylation reaction. For example, carbonylation processes often introduce hydrogen iodide to the reaction medium, which may subsequently form methyl iodide.

Carbonylation reaction conditions may vary depending upon reaction parameters, reactor size and charge and the individual components employed. In some embodiments, the carbonylation processes described herein may be one or more batch or continuous processes and the carbonylation conditions may include a carbonylation pressure in a range of 200 psig (1379 kPa) to 2000 psig (13790 kPa), or 200 psig (1379 kPa) to 1000 psig (6895 kPa), or 300 psig (2068 kPa) to 500 psig (3447 kPa), for example, and a carbonylation temperature in a range of 150° C. to 250° C., or 170° C. to 220° C., or 150° C. to 200° C.

The carbonylation product generally includes an acetic acid product. In addition to the acetic acid, the carbonylation product generally includes one or more impurities. Impurities are defined herein as any component in a process stream other than the targeted product itself (e.g., acetic acid is the targeted product in the carbonylation product stream). For example, the impurities present in carbonylation product stream may include water, aldehydes (e.g., acetaldehyde, crotonaldehyde, butyraldehyde and derivatives thereof), alkanes, formic acid, methyl formate or combinations thereof as well as additional compounds other than the acetic acid, depending on the specific process.

It can be desirable to separate such impurities from the acetic acid prior to use of the acetic acid in subsequent processes. Such separation processes may include those known in the art and generally include separating one or more of the impurities from the acetic acid within a process stream (wherein the process stream may be referred to as "impure acetic acid") to form purified acetic acid via one or more methods, including, but not limited to, extraction, distillation, extractive distillation, caustic treatment, scavenging, adsorption and combinations thereof, for example. As used herein, the term "purified acetic acid" generally refers to an acetic acid stream having a concentration of one or more impurities that is reduced in comparison to that impurity's concentration in the impure acetic acid. It is to be noted that use of the term "acetic acid stream" herein refers to any stream containing acetic acid. The specific components and concentrations in the respective acetic acid stream will be clear based on the referenced discussion thereof.

While many processes exist for the separation of the impurities, such processes can be difficult to implement, ineffective and costly. Thus, continuous efforts have been underway to improve and develop methods to separate these impurities from acetic acid. Historically, such efforts have included converting acetaldehyde to one or more compounds that are more easily separated from the remaining components than acetaldehyde. For example, the acetaldehyde can be converted to paraldehyde. Paraldehyde has a higher boiling than acetaldehyde, may be more easily separated than acetaldehyde and decomposes when heated above 60° C. Thus, it is desirable to avoid paraldehyde formation. However, crotonaldehyde is stable at such temperatures and has a sufficiently high boiling point to be removed from the acetic acid efficiently by distillation. Thus, it is desirable to convert acetaldehyde to crotonaldehyde while avoiding paraldehyde formation. The embodiments described herein are capable of such conversion.

Thus, one or more embodiments include contacting at least a portion of the carbonylation product (or a derivative thereof) with a micro-porous material at conversion conditions sufficient to convert at least a portion of the acetaldehyde present in the stream being contacted to crotonaldehyde. For example, such contact may result in an acetaldehyde to crotonaldehyde conversion of at least 60%, or at least 70%, or at least 80%, or at least 85%, or at least 90%, or at least 95%, or at least 98%. Such contact may result in an acetaldehyde to paraldehyde conversion of less than 5%, or less than 1% or less than 0.1%, for example. The term "micro-porous" as used herein refers to a material having an average pore diameter of less than 2 nanometers (nm).

In one more embodiments, the impure acetic acid stream may include acetaldehyde at a concentration in a range of less than 0.1 wt. % to 4.5 wt. %, or at least 3 wt. %, or 2.5 wt. % to 3.5 wt. % based on the total weight of the impure acetic acid stream.

In one more embodiments, the impure acetic acid stream may include water at a water concentration in a range of less than 2 wt. %, or less than 1 wt. %, or less than 0.5 wt. % based on the total weight of the impure acetic acid stream, for example.

In one or more embodiments, the micro-porous material includes a silicoaluminophosphate (SAPO). The SAPO may be generally represented by the formula $(SiO_2)_x(Al_2O_3)_y(P_2O_5)_z$, wherein x, y and z are measured and defined as mole fractions of the metal atom and thus x, y and z may be defined in terms of the following formula: $(Si_xAl_yP_z)O_2$, where x+y+z=1. During preparation of the SAPO, Si is substituted into an aluminophsophate framework and thus, in the resultant SAPO, y may be about 0.5 and x+z may be about 0.5, for example. Further examples of measurement of x, y and z can be found in "New Developments in Zeolite Science and Technology", React. Kinet. Catal. Lett, vol. 67, No. 2, 365-370 (1999), which is incorporated by reference herein.

As utilized herein, the silicoaluminophosphate (SAPO) materials include those having a one-dimensional framework with no cages. Further description of such micro-porous materials and their frameworks are discussed in "Methanol-to-Olefin Conversion on Silicoaluminophosphate Catalysts: Effect of Brönsted Acid Sites and Framework Structures," ACS Catalysis, vol. 1, 292-299 (2011), which is incorporated by reference herein.

The SAPO materials may have an average surface area in a range of at least 180 m²/g to 550 m²/g, or 200 m²/g to 400 m²/g. The SAPO materials may further have an average pore volume in a range of at least 0.16 cm³/g to 0.27 cm³/g, or 0.18 cm³/g to 0.20 cm³/g, for example.

In one or more embodiments, the SAPO materials exhibit a Brönsted acidity in a range of 0.05 mmol/g to 0.25 mmol/g, or less than 1 mmol/g, or 0.1 mmol/g to 0.2 mmol/g, for example. As used herein, the Brönsted acidity is measured as described in "Methanol-to-Olefin Conversion on Silicoaluminophosphate Catalysts: Effect of Brönsted Acid Sites and Framework Structures," ACS Catalysis, vol. 1, 292-299 (2011).

A variety of silicoaluminophosphates are commercially available, including but not limited to SAPO-34, SAPO-11, SAPO-5, SAPO-18, SAPO-41, SAPO-46 and SAPO-21. However, as demonstrated by the examples included herein, not all commercially available SAPO materials are capable of selective conversion as recited herein. In one or more embodiments, the micro-porous material is selected from SAPO-11, SAPO-41, SAPO 46 and combinations thereof. In another embodiment, the micro-porous material is selected from SAPO-41, SAPO-46 and combinations thereof.

At least a portion of the carbonylation product may contact the micro-porous material via methods known in the art. For example, the micro-porous material may be loaded within a reaction vessel and the at least a portion of the carbonylation product introduced thereto. The micro-porous material may be loaded into the reaction vessel in an amount in a range of 0.5 grams (g) to 10 g micro-porous material/g organic material, or 1 g to 8 g micro-porous material/g organic material, or 1.4 g to 6 g micro-porous material/g organic material, for example.

The conversion conditions vary depending upon a variety of factors. However, the conversion conditions are such that they promote conversion of acetaldehyde to crotonaldehyde but not paraldehyde (i.e., "selective conversion"). In one or more embodiments, the conversion temperature is therefore in a range of room temperature to the boiling point of acetaldehyde, for example. As used herein, "room temperature" means that a temperature difference of a few degrees does not matter to the phenomenon under investigation. In some environments, room temperature may include a temperature in a range of about 20° C. to about 28° C., including about 25° C., while in other environments, room temperature may include a temperature in a range of about 10° C. to about 32° C. However, room temperature measurements generally do not include close monitoring of the temperature of the process and therefore such a recitation does not intend to bind the embodiments described herein to any predetermined temperature range.

In one or more embodiments, components within the carbonylation product stream or at least a portion thereof may be separated from one another via flash separation into a liquid fraction and a vapor fraction. The liquid fraction may include residual carbonylation catalyst as well as other components, while the vapor fraction may include the acetic acid, unreacted reactants, water, methyl iodide and impurities generated during the carbonylation reaction. The liquid fraction may be recycled to the carbonylation reaction while the vapor fraction may undergo supplemental separation.

The supplemental separation may include a first column (e.g., a light ends distillation column) adapted to separate components of the liquid fraction and form a first overhead stream and an acetic acid stream. The first overhead stream may include methyl iodide, water, methanol, methyl acetate, impurities or combinations thereof. The acetic acid stream may be passed to a drying column to remove any water contained therein and then to a second column (e.g., a heavy ends distillation column) adapted to separate components of the acetic acid stream and form a second overhead stream and a bottoms stream. The second overhead stream may include methyl iodide, methyl acetate, acetic acid, water, impurities or combinations thereof.

The first overhead stream may be condensed and separated in a decanter to form a light, aqueous phase and a heavy, organic phase. The heavy, organic phase may include methyl iodide and aldehyde impurities. The light, aqueous phase may include one or more of water, acetic acid and methyl acetate. The light, aqueous phase may be recycled to the reactor or light ends distillation, for example.

Any stream or portion thereof containing target impurities may contact the micro-porous material to selectively convert such impurities. However, one or more embodiments include contacting the acetic acid stream with the micro-porous material. Alternative embodiments include contacting the heavy, organic phase with the micro-porous material.

The FIGURE illustrates a schematic of an embodiment of a specific, non-limiting embodiment of a carboxylic acid production process 100. The process 100 is generally described in terms of functional areas, i.e., a reaction area 102, a light-ends area 104, a purification area 106 and a recycle area 108, rather than specific process equipment. Note that the "streams" discussed herein may be part of more than one functional area.

The reaction area 102 may include a reactor 110, a flash vessel 120, equipment associated with the reactor 110 and flash vessel 120, and streams associated with the reactor 110 and flash vessel 120. For example, the reaction area 102 may include reactor 110, flash vessel 120, and streams (or portions of streams) 111, 112, 114, 121, 126, 131, 160, 138, 139, 148. The reactor 110 is a reactor or vessel in which an alcohol is carbonylated in the presence of a carbonylation catalyst to form a carboxylic acid at elevated pressure and temperature. The flash vessel 120 is a tank or vessel in which a reaction mixture obtained in the reactor, for example the reactor 110, is at least partially depressurized and/or cooled to form a vapor stream and a liquid stream.

The light-ends area 104 may include a separation column, for example, a light-ends column 130, equipment associated with the light-ends column 130, and streams associated with the light-ends column 130. For example, the light-ends area 104 may include the light-ends column 130, the decanter 134, and streams 126, 131, 132, 133, 135, 136, 138, 139, 160. The light-ends column 130 is a fractioning or distillation column and includes any equipment associated with the column, including but not limited to heat exchangers, decanters, pumps, compressors, valves, and the like.

The purification area 106 may include a drying column 140, optionally, a heavy-ends column 150, equipment associated with the drying column 140 and the heavy-ends column 150, and streams associated with the drying column 140 and the heavy-ends column 150. For example, the purification area 106 may include the drying column 140, the heavy-ends column 150, and streams 136, 141, 142, 145, 148, 151, 152, 156. The heavy-ends column 150 is a fractioning or distillation column and includes any equipment associated with the column, including but not limited to heat exchangers, decanters, pumps, compressors, valves, and the like.

The recycle area 108 may include process streams recycled to the reaction area 102 and/or light-ends area 104. For example, in the FIGURE, the recycle area 108 may include streams 121, 138, 139, 148.

In one or more embodiments, the reactor 110 may be configured to receive a carbon monoxide feed stream 114 and a methanol or a methanol/methyl acetate feed stream 112. A reaction mixture may be withdrawn from the reactor in the stream 111. Other streams may be included, for example, a stream that may recycle a bottoms mixture of the reactor 110 back into the reactor 110, or a stream may be included to release a gas from the reactor 110. The stream 111 may include at least a part of the reaction mixture.

In one or more embodiments, the flash vessel 120 may be configured to receive stream 111 from the reactor 110. In the flash vessel 120, the stream 111 may be separated into a vapor stream 126 and a liquid stream 121. The vapor stream 126 may be communicated to the light-ends column 130, and the liquid stream 121 may be communicated to the reactor 110 (the stream 121 may thus be considered in the recycle area 108 and in the reactor area 102). In one or more embodiments, the stream 126 may include acetic acid, water, methyl iodide (MeI), methyl acetate, hydrogen iodide (HI), and mixtures thereof.

In an embodiment, the light-ends column 130 may include a distillation column and equipment associated with the distillation column including but not limited to a heat exchanger 137, a decanter 134, pumps, compressors, valves, and other related equipment. The light-ends column 130 may be configured to receive stream 126 from the flash vessel 120. The stream 132 includes overhead product from the light-ends column 130, and the stream 131 includes the bottoms product from the light-ends column 130. The light-ends column 130 may include a decanter 134, and the stream 132 may pass into the decanter 134.

The stream 135 may emit from the decanter 134 and recycle back to the light-ends column 130. The stream 138 may emit from the decanter 134 and may recycle back to the reactor 110 via, for example, the stream 112 or be combined with any of the other streams that feed the reactor (the stream 138 may thus be considered in the recycle area 108, in the light-ends area 104, and in the reactor area 102). The stream 139 may recycle a portion of the light phase of decanter 134 back to the reactor 110 via, for example, the stream 112 (the stream 139 may thus be considered in the recycle area 108, in the light-ends area 104, and in the reactor area 102). The stream 136 may emit from the light-ends column 130. Other streams may be included, for example, a stream that may recycle a bottoms mixture of the light-ends column 130 back into the light-ends column 130. Any stream received by or emitted from the light-ends column 130 may pass through a pump, compressor, heat exchanger, and the like as is common in the art.

In an embodiment, the drying column 140 may include a vessel and equipment associated with the vessel including but not limited to heat exchangers, decanters, pumps, compressors, valves, and the like. The drying column 140 may be configured to receive stream 136 from the light-ends column 130. The drying column 140 may separate components of stream 136 into streams 142 and 141.

The stream 142 may emit from the drying column 140, recycle back to the drying column via the stream 145, and/or recycle back to the reactor 110 through the stream 148 (via, for example, the stream 112). The stream 141 may emit from the drying column 140 and may include a de-watered crude acetic acid product. The stream 142 may pass through equipment that is readily available, for example, a heat exchanger or separation vessel before streams 145 or 148 recycle components of the stream 142. Other streams may be included, for example, a stream may recycle a bottoms mixture of the drying column 140 back into the drying column 140. Any stream received by or emitted from the drying column 140 may pass through a pump, compressor, heat exchanger, separation vessel, and the like as is common in the art.

The heavy-ends column 150 may include a distillation column and equipment associated with the distillation column including but not limited to heat exchangers, decanters, pumps, compressors, valves, and the like. The heavy-ends column 150 may be configured to receive the stream 141 from the drying column 140. The heavy-ends column 150 may separate components from the stream 141 into streams 151, 152, and 156. Streams 151 and 152 may be sent to additional processing equipment (not shown) for further processing. The stream 152 may also be recycled, for example, to light-ends column 140. The stream 156 may include an acetic acid product.

The purification area 106 may further include a reaction vessel 200 having the micro-porous material disposed therein. A variety of the streams may be passed through the micro-porous material prior to proceeding downstream. For example, the stream 138 may be passed through the reaction vessel 200 via the stream 138a to form the stream 138b. Alternatively, or combination therewith, the stream 141 may be passed through the reaction vessel 200 via the stream 141a to form the stream 141b.

Suitable alternative embodiments for the carboxylic acid production system 100 may be found in U.S. Pat. No. 6,552,221, which is incorporated by reference in its entirety.

EXAMPLES

To facilitate a better understanding of the disclosure, the following examples of embodiments are given. In no way should the following examples be read to limit, or to define, the scope of the appended claims.

Slurries of various porous materials in acetaldehyde (HAc) and methyl iodide (MeI) as the bulk solvent were prepared. The resultant slurries were sampled periodically for Fourier transform infrared spectroscopy (FTIR) analysis. The results follow in Table 1.

TABLE 1

| Porous Material (PM) | Loading (g PM/g HAc) | Time (min) | Hac (wt. %) | Croton-aldehyde (wt. %) | Paraldehyde (wt. %) |
|---|---|---|---|---|---|
| Amberlyst ®15 | 10.5 | 1 | 17.3 | 7.8 | 74.9 |
| Amberlyst ®15 | 10.5 | 7 | 9.8 | 36.3 | 53.9 |
| Amberlyst ®15 | 10.5 | 12 | 7.3 | 51.8 | 40.9 |
| Amberlyst ®15 | 10.5 | 20 | 7.4 | 60.2 | 32.4 |
| Amberlyst ®15 | 10.5 | 35 | 6.9 | 67.6 | 25.5 |
| Amberlyst ®15 | 10.5 | 55 | 4.5 | 75.1 | 20.4 |
| Amberlyst ®15 | 10.5 | 110 | 2.9 | 84.8 | 12.3 |
| Y-zeolite | 8.4 | 1 | 71.4 | N/A | 28.6 |
| Y-zeolite | 8.4 | 10 | 67.4 | N/A | 32.6 |
| Y-zeolite | 8.4 | 40 | 65 | N/A | 35 |
| Y-zeolite | 8.4 | 123 | 63.5 | N/A | 36.5 |
| Y-zeolite | 8.4 | 196 | 60.3 | N/A | 39.7 |
| SAPO-11 | 0.83 | 1.2 | 89.6 | 10.4 | N/A |
| SAPO-11 | 0.83 | 138 | 79.9 | 20.1 | N/A |
| SAPO-11 | 0.83 | 1440 | 51.7 | 48.3 | N/A |
| SAPO-11 | 1.83 | 1.2 | 94.2 | 5.8 | N/A |
| SAPO-11 | 1.83 | 138 | 79.4 | 20.6 | N/A |
| SAPO-11 | 1.83 | 1440 | 46 | 54 | N/A |
| SAPO-11 | 2.44 | 1.2 | 95.5 | 4.5 | N/A |
| SAPO-11 | 2.44 | 138 | 74.3 | 25.7 | N/A |
| SAPO-11 | 2.44 | 1440 | 34.1 | 65.9 | N/A |
| SAPO-11 | 6.11 | 1.2 | 99.9 | 0.1 | N/A |
| SAPO-11 | 6.11 | 138 | 53.7 | 46.3 | N/A |
| SAPO-11 | 6.11 | 1440 | 21.1 | 78.8 | N/A |
| SAPO-05 | 0.67 | 1.2 | 91.9 | N/A | N/A |
| SAPO-05 | 0.67 | 138 | 87.1 | N/A | N/A |
| SAPO-05 | 0.67 | 1440 | 56.3 | N/A | N/A |
| SAPO-05 | 1.66 | 1.2 | 87.2 | N/A | N/A |
| SAPO-05 | 1.66 | 138 | 75.3 | N/A | N/A |
| SAPO-05 | 1.66 | 1440 | 62.2 | N/A | N/A |
| SAPO-05 | 2.99 | 1.2 | 88.7 | N/A | N/A |
| SAPO-05 | 2.99 | 138 | 91.2 | N/A | N/A |
| SAPO-05 | 2.99 | 1440 | 59.2 | N/A | N/A |
| SAPO-05 | 6.6 | 1.2 | 97.1 | N/A | N/A |
| SAPO-05 | 6.6 | 138 | 80.6 | N/A | N/A |

It was observed that Amberlyst® 15 reacted to produce both crotonaldehyde and paraldehyde by-products while Y-zeolite reacted to form paraldehyde and not crotonaldehyde. Alternatively, SAPO-11 reacted to form crotonaldehyde and not paraldehyde. However, it was observed that SAPO-05 did not react but rather slowly adsorbed HAc.

What is claimed is:
1. A process comprising:
   contacting methanol and carbon monoxide in the presence of a liquid reaction medium under carbonylation conditions sufficient to form a carbonylation product comprising acetic acid and acetaldehyde, wherein the liquid reaction medium comprises:
      a carbonylation catalyst selected from rhodium catalysts, iridium catalysts and palladium catalysts; and a water concentration of 1-14 wt. % based on the total weight of the liquid reaction medium; and contacting at least a portion of the carbonylation product with a micro-porous material to selectively convert at least a portion of the acetaldehyde to crotonaldehyde, wherein the micro-porous material comprises a silicoaluminophosphate (SAPO) comprising an average surface area in a range of 180-550 $m^2/g$ and a one-dimensional framework of pores absent cages, and wherein the selective conversion exhibits an acetaldehyde to paraldehyde conversion of less than 1% and an acetaldehyde to crotonaldehyde conversion of at least 85%.

2. The process of claim 1, wherein the micro-porous material is represented by the formula $(SiO_2)_x(Al_2O_3)_y(P_2O_5)_z$, where x+y+z=1.

3. The process of claim 1, wherein the selective conversion exhibits an acetaldehyde to crotonaldehyde conversion of at least 90%.

4. The process of claim 1, wherein the selective conversion exhibits an acetaldehyde to crotonaldehyde conversion of at least 95%.

5. The process of claim 1, wherein the selective conversion exhibits an acetaldehyde to paraldehyde conversion of less than 1%.

6. The process of claim 1, wherein the selective conversion does not comprise the conversion of acetaldehyde to paraldehyde.

7. The process of claim 1, wherein the micro-porous material comprises an average pore volume in a range of 0.16-0.27 $cm^3/g$.

8. The process of claim 1, wherein the micro-porous material comprises a one-dimensional framework of pores absent cages.

9. The process of claim 1, wherein the conversion conditions comprise a conversion temperature of about room temperature.

10. The process of claim 1, wherein the at least a portion of the carbonylation product comprises less than 1 wt. % water.

11. The process of claim 1, wherein the micro-porous material is selected from SAPO-11, SAPO-41, SAPO-46 and combinations thereof.

* * * * *